US009056167B2

(12) United States Patent
Pesach et al.

(10) Patent No.: US 9,056,167 B2
(45) Date of Patent: *Jun. 16, 2015

(54) METHOD AND DEVICE FOR DRUG DELIVERY

(71) Applicant: Insuline Medical Ltd., Petach-Tikva (IL)

(72) Inventors: Benny Pesach, Rosh-Ha'ayin (IL); Gabriel Bitton, Jerusalem (IL); Ron Nagar, Tel Aviv-Yafo (IL); Ram Weiss, Haifa (IL)

(73) Assignee: Insuline Medical Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,259

(22) Filed: Mar. 19, 2013

(65) Prior Publication Data

US 2013/0226079 A1 Aug. 29, 2013

Related U.S. Application Data

(63) Continuation of application No. 12/809,425, filed as application No. PCT/IB2008/003547 on Dec. 18, 2008, now Pat. No. 8,409,133.

(60) Provisional application No. 61/008,276, filed on Dec. 18, 2007.

(51) Int. Cl.
*A61N 1/08* (2006.01)
*A61M 5/172* (2006.01)
*A61M 5/142* (2006.01)

(52) U.S. Cl.
CPC .......... *A61M 5/1723* (2013.01); *A61M 5/14248* (2013.01); *A61M 2005/14296* (2013.01);

(Continued)

(58) Field of Classification Search
CPC .......... A61M 5/14248; A61M 5/1723; A61M 2005/14296; A61M 2005/1726
USPC .................................................... 604/65–67
See application file for complete search history.

(56) References Cited

U.S. PATENT DOCUMENTS 3,620,209 A 11/1971 Kravitz
3,683,911 A 8/1972 McCormick (Continued)

FOREIGN PATENT DOCUMENTS

EP 1611848 A1 1/2006
EP 1695664 A1 8/2006

(Continued)

OTHER PUBLICATIONS

Belinda et. al., (1996), Journal of Physiology, 572.3:811-820.

(Continued)

*Primary Examiner* — Laura Bouchelle
(74) *Attorney, Agent, or Firm* — Cooley LLP; Brian P. Hopkins

(57) ABSTRACT

An apparatus and a system for controlling and/or managing administration of a drug to a body of a patient. The apparatus includes a drug infusion device configured to deliver drug at a predetermined location in the body of the patient, at least one sensor disposed in the drug infusion device and configured to measure a. corresponding property related to the patient and selected from the group consisting of physiological properties, biochemical properties, environmental properties and drug-related properties, a controller disposed in the drug infusion device and configured to receive from the at least one sensor data representative of the measured corresponding property and based on the received data, determine a drug delivery rate. The drug delivery device is configured to deliver the drug to the body of the patient based on the determined drug delivery rate.

9 Claims, 8 Drawing Sheets

(52) U.S. Cl.
CPC .............. *A61M2005/1726* (2013.01); *A61M 2205/3368* (2013.01); *A61M 2205/50* (2013.01); *A61M 2205/60* (2013.01); *A61M 2230/201* (2013.01); *A61M 2230/50* (2013.01); *A61M 2230/63* (2013.01)

(56) References Cited

U.S. PATENT DOCUMENTS

| | | |
|---|---|---|
| 4,230,105 A | 10/1980 | Harwood |
| 4,628,928 A | 12/1986 | Lowell |
| 4,685,911 A | 8/1987 | Konno et al. |
| 4,744,787 A | 5/1988 | Phipps et al. |
| 4,747,819 A | 5/1988 | Phipps et al. |
| 4,771,772 A | 9/1988 | DeWitt |
| 4,898,592 A | 2/1990 | Latzke et al. |
| 4,948,587 A | 8/1990 | Kost et al. |
| 4,963,360 A | 10/1990 | Argaud |
| 4,987,897 A | 1/1991 | Funke |
| 4,998,930 A | 3/1991 | Lundahl |
| 5,047,007 A | 9/1991 | McNichols et al. |
| 5,053,033 A | 10/1991 | Clarke |
| 5,098,429 A | 3/1992 | Sterzer |
| 5,113,859 A | 5/1992 | Funke |
| 5,135,477 A | 8/1992 | Untereker et al. |
| 5,213,568 A | 5/1993 | Lattin et al. |
| 5,243,986 A | 9/1993 | Wurster |
| 5,271,736 A | 12/1993 | Picha |
| 5,306,252 A | 4/1994 | Yutori et al. |
| 5,307,816 A | 5/1994 | Hashimoto et al. |
| 5,324,521 A | 6/1994 | Gertner et al. |
| 5,332,577 A | 7/1994 | Gertner et al. |
| 5,354,324 A | 10/1994 | Gregory |
| 5,378,475 A | 1/1995 | Smith et al. |
| 5,383,873 A | 1/1995 | Hoey et al. |
| 5,411,550 A | 5/1995 | Herweck et al. |
| 5,430,016 A | 7/1995 | Balschmidt et al. |
| 5,498,254 A | 3/1996 | Hoey et al. |
| 5,512,048 A | 4/1996 | Slettenmark |
| 5,523,092 A | 6/1996 | Hanson et al. |
| 5,525,356 A | 6/1996 | Jevne et al. |
| 5,527,292 A | 6/1996 | Adams et al. |
| 5,545,208 A | 8/1996 | Wolff et al. |
| 5,556,421 A | 9/1996 | Prutchi et al. |
| 5,564,439 A | 10/1996 | Picha |
| 5,567,592 A | 10/1996 | Benet et al. |
| 5,571,152 A | 11/1996 | Chen et al. |
| 5,590,657 A | 1/1997 | Cain et al. |
| 5,591,445 A | 1/1997 | Hoey et al. |
| 5,634,468 A | 6/1997 | Platt et al. |
| 5,658,583 A | 8/1997 | Zhang et al. |
| 5,706,807 A | 1/1998 | Picha |
| 5,713,847 A | 2/1998 | Howard, III et al. |
| 5,725,017 A | 3/1998 | Elsberry et al. |
| 5,725,567 A | 3/1998 | Wolff et al. |
| 5,730,125 A | 3/1998 | Prutchi et al. |
| 5,741,211 A | 4/1998 | Renirie et al. |
| 5,798,065 A | 8/1998 | Picha |
| 5,843,051 A | 12/1998 | Adams et al. |
| 5,851,217 A | 12/1998 | Wolff et al. |
| 5,851,231 A | 12/1998 | Wolff et al. |
| 5,871,446 A | 2/1999 | Wilk |
| 5,871,535 A | 2/1999 | Wolff et al. |
| 5,882,332 A | 3/1999 | Wijay |
| 5,919,216 A | 7/1999 | Houben et al. |
| 5,919,479 A | 7/1999 | Zhang et al. |
| 5,997,468 A | 12/1999 | Wolff et al. |
| 6,004,346 A | 12/1999 | Wolff et al. |
| 6,004,927 A | 12/1999 | Benet et al. |
| 6,026,316 A | 2/2000 | Kucharczyk et al. |
| 6,028,054 A | 2/2000 | Benet et al. |
| 6,043,273 A | 3/2000 | Duhaylongsod |
| 6,060,454 A | 5/2000 | Duhaylongsod |
| 6,061,587 A | 5/2000 | Kucharczyk et al. |
| 6,087,394 A | 7/2000 | Duhaylongsod |
| 6,093,167 A | 7/2000 | Houben et al. |
| 6,101,412 A | 8/2000 | Duhaylongsod |
| 6,122,536 A | 9/2000 | Sun et al. |
| 6,125,290 A | 9/2000 | Miesel |
| 6,125,291 A | 9/2000 | Miesel et al. |
| 6,127,117 A | 10/2000 | Morris et al. |
| 6,127,410 A | 10/2000 | Duhaylongsod |
| 6,133,242 A | 10/2000 | Zalewski et al. |
| 6,134,459 A | 10/2000 | Roberts et al. |
| 6,135,978 A | 10/2000 | Houben et al. |
| 6,141,589 A | 10/2000 | Duhaylongsod |
| 6,144,866 A | 11/2000 | Miesel et al. |
| 6,152,898 A | 11/2000 | Olsen |
| 6,156,029 A | 12/2000 | Mueller |
| 6,161,047 A | 12/2000 | King et al. |
| 6,198,952 B1 | 3/2001 | Miesel |
| 6,198,966 B1 | 3/2001 | Heruth |
| 6,210,368 B1 | 4/2001 | Rogers |
| 6,228,050 B1 | 5/2001 | Olsen et al. |
| 6,228,595 B1 | 5/2001 | Morris et al. |
| 6,238,367 B1 | 5/2001 | Christiansen et al. |
| 6,245,347 B1 | 6/2001 | Zhang et al. |
| 6,247,812 B1 | 6/2001 | Miehle et al. |
| 6,254,598 B1 | 7/2001 | Edwards et al. |
| 6,261,280 B1 | 7/2001 | Houben et al. |
| 6,261,595 B1 | 7/2001 | Stanley et al. |
| 6,269,340 B1 | 7/2001 | Ford et al. |
| 6,283,949 B1 | 9/2001 | Roorda |
| 6,284,266 B1 | 9/2001 | Zhang et al. |
| 6,292,702 B1 | 9/2001 | King et al. |
| 6,296,630 B1 | 10/2001 | Altman et al. |
| 6,303,142 B1 | 10/2001 | Zhang et al. |
| 6,305,381 B1 | 10/2001 | Weijand et al. |
| 6,306,431 B1 | 10/2001 | Zhang et al. |
| 6,312,412 B1 | 11/2001 | Saied et al. |
| 6,323,184 B1 | 11/2001 | Zalewski et al. |
| 6,338,850 B1 | 1/2002 | Jevnikar et al. |
| 6,340,472 B1 | 1/2002 | Zhang et al. |
| 6,342,250 B1 | 1/2002 | Masters |
| 6,350,276 B1 | 2/2002 | Knowlton |
| 6,375,628 B1 | 4/2002 | Zadno-Azizi et al. |
| 6,377,846 B1 | 4/2002 | Chornenky et al. |
| 6,379,382 B1 | 4/2002 | Yang |
| 6,385,491 B1 | 5/2002 | Lindemans et al. |
| 6,389,313 B1 | 5/2002 | Marchitto et al. |
| 6,395,015 B1 | 5/2002 | Borst et al. |
| 6,414,018 B1 | 7/2002 | Duhaylongsod |
| 6,416,510 B1 | 7/2002 | Altman et al. |
| 6,425,853 B1 | 7/2002 | Edwards |
| 6,427,088 B1 | 7/2002 | Bowman, IV et al. |
| 6,442,435 B2 | 8/2002 | King et al. |
| 6,447,443 B1 | 9/2002 | Keogh et al. |
| 6,449,507 B1 | 9/2002 | Hill et al. |
| 6,453,195 B1 | 9/2002 | Thompson |
| 6,453,648 B1 | 9/2002 | Zhang et al. |
| 6,456,883 B1 | 9/2002 | Torgerson et al. |
| 6,458,102 B1 | 10/2002 | Mann et al. |
| 6,458,118 B1 | 10/2002 | Lent et al. |
| 6,461,329 B1 | 10/2002 | Van Antwerp et al. |
| 6,465,006 B1 | 10/2002 | Zhang et al. |
| 6,465,709 B1 | 10/2002 | Sun et al. |
| 6,471,675 B1 | 10/2002 | Rogers et al. |
| 6,471,689 B1 | 10/2002 | Joseph et al. |
| 6,482,214 B1 | 11/2002 | Sidor, Jr. et al. |
| 6,485,464 B1 | 11/2002 | Christenson et al. |
| 6,487,446 B1 | 11/2002 | Hill et al. |
| 6,488,959 B2 | 12/2002 | Stanley et al. |
| 6,511,428 B1 | 1/2003 | Azuma et al. |
| 6,512,958 B1 | 1/2003 | Swoyer et al. |
| 6,528,086 B2 | 3/2003 | Zhang |
| 6,532,388 B1 | 3/2003 | Hill et al. |
| 6,537,242 B1 | 3/2003 | Palmer |
| 6,542,350 B1 | 4/2003 | Rogers |
| 6,544,212 B2 | 4/2003 | Galley et al. |
| 6,546,281 B1 | 4/2003 | Zhang et al. |
| 6,551,276 B1 | 4/2003 | Mann et al. |
| 6,551,346 B2 | 4/2003 | Crossley |
| 6,554,798 B1 | 4/2003 | Mann et al. |
| 6,558,345 B1 | 5/2003 | Houben et al. |
| 6,558,382 B2 | 5/2003 | Jahns et al. |

(56) References Cited

U.S. PATENT DOCUMENTS

| | | |
|---|---|---|
| 6,562,001 B2 | 5/2003 | Lebel et al. |
| 6,564,105 B2 | 5/2003 | Starkweather et al. |
| 6,571,125 B2 | 5/2003 | Thompson |
| 6,572,542 B1 | 6/2003 | Houben et al. |
| 6,572,583 B1 | 6/2003 | Olsen et al. |
| 6,577,899 B2 | 6/2003 | Lebel et al. |
| 6,584,335 B1 | 6/2003 | Haar et al. |
| 6,584,360 B2 | 6/2003 | Francischelli et al. |
| 6,585,644 B2 | 7/2003 | Lebel et al. |
| 6,585,707 B2 | 7/2003 | Cabiri et al. |
| 6,592,519 B1 | 7/2003 | Martinez |
| 6,597,946 B2 | 7/2003 | Avrahami et al. |
| 6,605,039 B2 | 8/2003 | Houben et al. |
| 6,613,082 B2 | 9/2003 | Yang |
| 6,613,084 B2 | 9/2003 | Yang |
| 6,613,350 B1 | 9/2003 | Zhang et al. |
| 6,615,083 B2 | 9/2003 | Kupper |
| 6,620,151 B2 | 9/2003 | Blischak et al. |
| 6,622,731 B2 | 9/2003 | Daniel et al. |
| 6,626,867 B1 | 9/2003 | Christenson et al. |
| 6,628,987 B1 | 9/2003 | Hill et al. |
| 6,628,989 B1 | 9/2003 | Penner et al. |
| 6,635,167 B1 | 10/2003 | Richards et al. |
| 6,644,321 B1 | 11/2003 | Behm |
| 6,645,176 B1 | 11/2003 | Christenson et al. |
| 6,647,299 B2 | 11/2003 | Bourget |
| 6,648,821 B2 | 11/2003 | Lebel et al. |
| 6,650,935 B1 | 11/2003 | Watmough |
| 6,659,948 B2 | 12/2003 | Lebel et al. |
| 6,669,663 B1 | 12/2003 | Thompson |
| 6,673,070 B2 | 1/2004 | Edwards et al. |
| 6,673,596 B1 | 1/2004 | Sayler et al. |
| 6,675,049 B2 | 1/2004 | Thompson et al. |
| 6,681,135 B1 | 1/2004 | Davis et al. |
| 6,685,452 B2 | 2/2004 | Christiansen et al. |
| 6,687,546 B2 | 2/2004 | Lebel et al. |
| 6,690,973 B2 | 2/2004 | Hill et al. |
| 6,694,191 B2 | 2/2004 | Starkweather et al. |
| 6,697,667 B1 | 2/2004 | Lee et al. |
| 6,706,038 B2 | 3/2004 | Francischelli et al. |
| 6,711,436 B1 | 3/2004 | Duhaylongsod |
| 6,714,822 B2 | 3/2004 | King et al. |
| 6,716,178 B1 | 4/2004 | Kilpatrick et al. |
| 6,718,208 B2 | 4/2004 | Hill et al. |
| 6,723,087 B2 | 4/2004 | O'Neill et al. |
| 6,726,673 B1 | 4/2004 | Zhang et al. |
| 6,728,574 B2 | 4/2004 | Ujhelyi et al. |
| 6,733,446 B2 | 5/2004 | Lebel et al. |
| 6,733,474 B2 | 5/2004 | Kusleika |
| 6,733,476 B2 | 5/2004 | Christenson et al. |
| 6,733,500 B2 | 5/2004 | Kelley et al. |
| 6,735,471 B2 | 5/2004 | Hill et al. |
| 6,736,789 B1 | 5/2004 | Spickermann |
| 6,736,797 B1 | 5/2004 | Larsen et al. |
| 6,738,671 B2 | 5/2004 | Christophersom et al. |
| 6,740,075 B2 | 5/2004 | Lebel et al. |
| 6,743,204 B2 | 6/2004 | Christenson et al. |
| 6,743,227 B2 | 6/2004 | Seraj et al. |
| 6,744,350 B2 | 6/2004 | Blomquist |
| 6,748,653 B2 | 6/2004 | Lindemans et al. |
| 6,752,155 B2 | 6/2004 | Behm |
| 6,755,849 B1 | 6/2004 | Gowda et al. |
| 6,756,053 B2 | 6/2004 | Zhang et al. |
| 6,758,810 B2 | 7/2004 | Lebel et al. |
| 6,758,828 B2 | 7/2004 | Conroy et al. |
| 6,764,446 B2 | 7/2004 | Wolinsky et al. |
| 6,766,183 B2 | 7/2004 | Walsh et al. |
| 6,780,426 B2 | 8/2004 | Zhang et al. |
| 6,799,149 B2 | 9/2004 | Hartlaub |
| 6,804,558 B2 | 10/2004 | Haller et al. |
| 6,805,667 B2 | 10/2004 | Christopherson et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,823,213 B1 | 11/2004 | Norris et al. |
| 6,827,702 B2 | 12/2004 | Lebel et al. |
| 6,836,687 B2 | 12/2004 | Kelley et al. |
| 6,846,823 B2 | 1/2005 | Landau et al. |
| 6,852,104 B2 | 2/2005 | Blomquist |
| 6,852,694 B2 | 2/2005 | Van Antwerp et al. |
| 6,865,419 B2 | 3/2005 | Mulligan et al. |
| 6,866,678 B2 | 3/2005 | Shenderova et al. |
| 6,872,200 B2 | 3/2005 | Mann et al. |
| 6,873,268 B2 | 3/2005 | Lebel et al. |
| 6,878,529 B2 | 4/2005 | Harrow et al. |
| 6,887,238 B2 | 5/2005 | Jahns et al. |
| 6,904,318 B2 | 6/2005 | Hill et al. |
| 6,913,763 B2 | 7/2005 | Lerner |
| 6,915,157 B2 | 7/2005 | Bennett et al. |
| 6,922,585 B2 | 7/2005 | Zhou et al. |
| 6,923,784 B2 | 8/2005 | Stein |
| 6,925,393 B1 | 8/2005 | Kalatz et al. |
| 6,927,246 B2 | 8/2005 | Noronha et al. |
| 6,928,338 B1 | 8/2005 | Buchser et al. |
| 6,930,602 B2 | 8/2005 | Villaseca et al. |
| 6,936,029 B2 | 8/2005 | Mann et al. |
| 6,950,708 B2 | 9/2005 | Bowman, IV et al. |
| 6,955,661 B1 | 10/2005 | Herweck et al. |
| 6,955,819 B2 | 10/2005 | Zhang et al. |
| 6,958,705 B2 | 10/2005 | Lebel et al. |
| 6,961,448 B2 | 11/2005 | Nichols et al. |
| 6,962,584 B1 | 11/2005 | Stone et al. |
| 6,966,322 B2 | 11/2005 | McVenes et al. |
| 6,969,369 B2 | 11/2005 | Struble |
| 6,974,437 B2 | 12/2005 | Lebel et al. |
| 6,978,174 B2 | 12/2005 | Gelfand et al. |
| 6,979,315 B2 | 12/2005 | Rogers et al. |
| 6,979,326 B2 | 12/2005 | Mann et al. |
| 6,979,351 B2 | 12/2005 | Forsell et al. |
| 6,984,229 B2 | 1/2006 | Neuberger |
| 6,985,768 B2 | 1/2006 | Hemming et al. |
| 6,991,916 B2 | 1/2006 | Benson et al. |
| 6,997,920 B2 | 2/2006 | Mann et al. |
| 7,011,630 B2 | 3/2006 | Desai et al. |
| 7,013,177 B1 | 3/2006 | Whitehurst et al. |
| 7,018,384 B2 | 3/2006 | Skakoon |
| 7,018,568 B2 | 3/2006 | Tierney |
| 7,024,236 B2 | 4/2006 | Ford et al. |
| 7,024,245 B2 | 4/2006 | Lebel et al. |
| 7,024,248 B2 | 4/2006 | Penner et al. |
| 7,025,743 B2 | 4/2006 | Mann et al. |
| 7,025,760 B2 | 4/2006 | Miller et al. |
| 7,027,856 B2 | 4/2006 | Zhou et al. |
| 7,027,871 B2 | 4/2006 | Burnes et al. |
| 7,033,338 B2 | 4/2006 | Vilks et al. |
| 7,041,704 B2 | 5/2006 | Burgard et al. |
| 7,044,082 B1 | 5/2006 | Hewett et al. |
| 7,052,483 B2 | 5/2006 | Wojcik |
| 7,054,782 B2 | 5/2006 | Hartlaub |
| 7,058,447 B2 | 6/2006 | Hill et al. |
| 7,063,684 B2 | 6/2006 | Moberg |
| 7,066,891 B2 | 6/2006 | Stadler et al. |
| 7,066,909 B1 | 6/2006 | Peter et al. |
| 7,069,078 B2 | 6/2006 | Houben |
| 7,072,802 B2 | 7/2006 | Hartlaub |
| 7,074,233 B1 | 7/2006 | Gowda et al. |
| 7,084,116 B2 | 8/2006 | Fraser et al. |
| 7,092,753 B2 | 8/2006 | Darvish et al. |
| 7,094,228 B2 | 8/2006 | Zhang et al. |
| 7,101,857 B2 | 9/2006 | Sung et al. |
| 7,107,086 B2 | 9/2006 | Reihl et al. |
| 7,107,093 B2 | 9/2006 | Burnes |
| 7,108,696 B2 | 9/2006 | Daniel et al. |
| 7,109,878 B2 | 9/2006 | Mann et al. |
| 7,115,606 B2 | 10/2006 | Landau et al. |
| 7,123,968 B2 | 10/2006 | Casscells, III et al. |
| 7,125,407 B2 | 10/2006 | Edwards et al. |
| 7,125,848 B2 | 10/2006 | Fraser et al. |
| 7,133,329 B2 | 11/2006 | Skyggebjerg et al. |
| 7,149,581 B2 | 12/2006 | Goedeke |
| 7,149,773 B2 | 12/2006 | Haller et al. |
| 7,150,975 B2 | 12/2006 | Tamada et al. |
| 7,151,961 B1 | 12/2006 | Whitehurst et al. |

(56) References Cited

U.S. PATENT DOCUMENTS

| | | |
|---|---|---|
| 7,160,252 B2 | 1/2007 | Cho et al. |
| 7,162,303 B2 | 1/2007 | Levin et al. |
| 7,162,307 B2 | 1/2007 | Patrias |
| 7,163,511 B2 | 1/2007 | Conn et al. |
| 7,164,948 B2 | 1/2007 | Struble et al. |
| 7,167,743 B2 | 1/2007 | Heruth et al. |
| 7,171,263 B2 | 1/2007 | Darvish et al. |
| 7,171,274 B2 | 1/2007 | Starkweather et al. |
| 7,179,226 B2 | 2/2007 | Crothall et al. |
| 7,181,505 B2 | 2/2007 | Haller et al. |
| 7,184,828 B2 | 2/2007 | Hill et al. |
| 7,184,829 B2 | 2/2007 | Hill et al. |
| 7,186,247 B2 | 3/2007 | Ujhelyi et al. |
| 7,187,979 B2 | 3/2007 | Haubrich et al. |
| 7,190,997 B1 | 3/2007 | Darvish et al. |
| 7,191,008 B2 | 3/2007 | Schmidt et al. |
| 7,193,521 B2 | 3/2007 | Moberg et al. |
| 7,203,541 B2 | 4/2007 | Sowelam et al. |
| 7,206,632 B2 | 4/2007 | King |
| 7,209,784 B2 | 4/2007 | Schmidt |
| 7,209,790 B2 | 4/2007 | Thompson et al. |
| 7,218,964 B2 | 5/2007 | Hill et al. |
| 8,409,133 B2 * | 4/2013 | Pesach et al. .................... 604/65 |
| 2001/0022279 A1 | 9/2001 | Denyer et al. |
| 2001/0047195 A1 | 11/2001 | Crossley |
| 2002/0026141 A1 | 2/2002 | Houben et al. |
| 2002/0032406 A1 | 3/2002 | Kusleika |
| 2002/0038101 A1 | 3/2002 | Avrahami et al. |
| 2002/0040208 A1 | 4/2002 | Flaherty et al. |
| 2002/0068869 A1 | 6/2002 | Brisken et al. |
| 2002/0072743 A1 | 6/2002 | KenKnight et al. |
| 2002/0077673 A1 | 6/2002 | Penner et al. |
| 2002/0082583 A1 | 6/2002 | Lerner |
| 2002/0082665 A1 | 6/2002 | Haller et al. |
| 2002/0102707 A1 | 8/2002 | Harrow et al. |
| 2002/0106410 A1 | 8/2002 | Masters |
| 2002/0133148 A1 | 9/2002 | Daniel et al. |
| 2002/0137014 A1 | 9/2002 | Anderson et al. |
| 2002/0176849 A1 | 11/2002 | Slepian |
| 2002/0177689 A1 | 11/2002 | Benson et al. |
| 2002/0177772 A1 | 11/2002 | Altman et al. |
| 2002/0177782 A1 | 11/2002 | Penner |
| 2002/0183682 A1 | 12/2002 | Darvish et al. |
| 2002/0183686 A1 | 12/2002 | Darvish et al. |
| 2003/0028089 A1 | 2/2003 | Galley et al. |
| 2003/0040683 A1 | 2/2003 | Rule et al. |
| 2003/0060753 A1 * | 3/2003 | Starkweather et al. ......... 604/66 |
| 2003/0060765 A1 | 3/2003 | Campbell et al. |
| 2003/0069614 A1 | 4/2003 | Bowman et al. |
| 2003/0073609 A1 | 4/2003 | Pinkerton |
| 2003/0100885 A1 | 5/2003 | Pettis et al. |
| 2003/0130616 A1 | 7/2003 | Steil et al. |
| 2003/0144712 A1 | 7/2003 | Streeter, M.D. |
| 2003/0167033 A1 | 9/2003 | Chen et al. |
| 2003/0171401 A1 | 9/2003 | Johnson et al. |
| 2003/0176933 A1 | 9/2003 | Lebel et al. |
| 2003/0181852 A1 | 9/2003 | Mann et al. |
| 2003/0181894 A1 | 9/2003 | Neuberger |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0208152 A1 | 11/2003 | Avrahami et al. |
| 2003/0212364 A1 | 11/2003 | Mann et al. |
| 2003/0212441 A1 | 11/2003 | Starkweather et al. |
| 2003/0231990 A1 | 12/2003 | Faries et al. |
| 2004/0014131 A1 | 1/2004 | Benson et al. |
| 2004/0024361 A1 | 2/2004 | Fago et al. |
| 2004/0028707 A1 | 2/2004 | Pinkerton |
| 2004/0030282 A1 | 2/2004 | Freyman et al. |
| 2004/0059328 A1 | 3/2004 | Daniel et al. |
| 2004/0062148 A1 | 4/2004 | Skyggebjerg et al. |
| 2004/0063200 A1 | 4/2004 | Chaikof et al. |
| 2004/0064086 A1 | 4/2004 | Gottlieb et al. |
| 2004/0064127 A1 | 4/2004 | Lerner |
| 2004/0064133 A1 | 4/2004 | Miller et al. |
| 2004/0073190 A1 | 4/2004 | Deem et al. |
| 2004/0082639 A1 | 4/2004 | Ho et al. |
| 2004/0085215 A1 | 5/2004 | Moberg et al. |
| 2004/0092885 A1 | 5/2004 | Duchon et al. |
| 2004/0098113 A1 | 5/2004 | Forsell et al. |
| 2004/0111132 A1 | 6/2004 | Shenderova et al. |
| 2004/0127895 A1 | 7/2004 | Flock et al. |
| 2004/0142034 A1 | 7/2004 | Thor et al. |
| 2004/0147872 A1 | 7/2004 | Thompson |
| 2004/0157884 A1 | 8/2004 | Johnson et al. |
| 2004/0171518 A1 | 9/2004 | Van Antwerp et al. |
| 2004/0186533 A1 | 9/2004 | Greenberg et al. |
| 2004/0193090 A1 | 9/2004 | Lebel et al. |
| 2004/0198822 A1 | 10/2004 | Fraser et al. |
| 2004/0202692 A1 | 10/2004 | Shanley et al. |
| 2004/0209869 A1 | 10/2004 | Landau et al. |
| 2004/0209960 A1 | 10/2004 | Burgard et al. |
| 2004/0210267 A1 | 10/2004 | Lebel et al. |
| 2004/0220551 A1 | 11/2004 | Flaherty et al. |
| 2004/0225338 A1 | 11/2004 | Lebel et al. |
| 2004/0230117 A1 | 11/2004 | Tosaya et al. |
| 2004/0236269 A1 | 11/2004 | Marchitto et al. |
| 2004/0248979 A1 | 12/2004 | Brettman et al. |
| 2004/0260239 A1 | 12/2004 | Kusleika |
| 2004/0265353 A1 | 12/2004 | Zhang et al. |
| 2005/0004663 A1 | 1/2005 | Llanos et al. |
| 2005/0008580 A1 | 1/2005 | Gong et al. |
| 2005/0009735 A1 | 1/2005 | Kim et al. |
| 2005/0015055 A1 | 1/2005 | Yang |
| 2005/0020577 A1 | 1/2005 | Landau et al. |
| 2005/0026909 A1 | 2/2005 | Landau et al. |
| 2005/0033148 A1 | 2/2005 | Haueter et al. |
| 2005/0033231 A1 | 2/2005 | Powell |
| 2005/0033370 A1 | 2/2005 | Jelen et al. |
| 2005/0054725 A1 | 3/2005 | Thor et al. |
| 2005/0059938 A1 | 3/2005 | Malisch |
| 2005/0065464 A1 | 3/2005 | Talbot et al. |
| 2005/0065465 A1 | 3/2005 | Lebel et al. |
| 2005/0065556 A1 | 3/2005 | Reghabi et al. |
| 2005/0084477 A1 | 4/2005 | Van Antwerp et al. |
| 2005/0090866 A1 | 4/2005 | Miller et al. |
| 2005/0107353 A1 | 5/2005 | Burgard et al. |
| 2005/0107738 A1 | 5/2005 | Slater et al. |
| 2005/0107743 A1 | 5/2005 | Fangrow |
| 2005/0113798 A1 | 5/2005 | Slater et al. |
| 2005/0124560 A1 | 6/2005 | Sung et al. |
| 2005/0137670 A1 | 6/2005 | Christopherson et al. |
| 2005/0143636 A1 | 6/2005 | Zhang et al. |
| 2005/0148955 A1 | 7/2005 | Chong et al. |
| 2005/0171160 A1 | 8/2005 | Edgar et al. |
| 2005/0171513 A1 | 8/2005 | Mann et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/0192637 A1 | 9/2005 | Girouard et al. |
| 2005/0196421 A1 | 9/2005 | Hunter et al. |
| 2005/0208095 A1 | 9/2005 | Hunter et al. |
| 2005/0217674 A1 | 10/2005 | Burton et al. |
| 2005/0220836 A1 | 10/2005 | Falotico et al. |
| 2005/0221270 A1 | 10/2005 | Connelly et al. |
| 2005/0222191 A1 | 10/2005 | Falotico et al. |
| 2005/0228049 A1 | 10/2005 | Thor et al. |
| 2005/0229931 A1 | 10/2005 | Denyer et al. |
| 2005/0232964 A1 | 10/2005 | Fennimore |
| 2005/0232965 A1 | 10/2005 | Falotico |
| 2005/0239838 A1 | 10/2005 | Edgar et al. |
| 2005/0239890 A1 | 10/2005 | Fraser et al. |
| 2005/0245840 A1 | 11/2005 | Christopherson et al. |
| 2005/0249775 A1 | 11/2005 | Falotico et al. |
| 2005/0249776 A1 | 11/2005 | Chen et al. |
| 2005/0256165 A1 | 11/2005 | Edgar et al. |
| 2005/0256499 A1 | 11/2005 | Pettis et al. |
| 2005/0267550 A1 | 12/2005 | Hess et al. |
| 2005/0270245 A1 | 12/2005 | Villaseca et al. |

(56) References Cited

U.S. PATENT DOCUMENTS

| | | |
|---|---|---|
| 2005/0272719 A1 | 12/2005 | Landau et al. |
| 2005/0272806 A1 | 12/2005 | Falotico et al. |
| 2005/0276842 A1 | 12/2005 | Zhang et al. |
| 2005/0282799 A1 | 12/2005 | Landau et al. |
| 2005/0282859 A1 | 12/2005 | Thor |
| 2006/0025663 A1 | 2/2006 | Talbot et al. |
| 2006/0025756 A1 | 2/2006 | Francischelli et al. |
| 2006/0030837 A1 | 2/2006 | McKenna et al. |
| 2006/0030838 A1 | 2/2006 | Gonnelli |
| 2006/0031094 A1 | 2/2006 | Cohen et al. |
| 2006/0063754 A1 | 3/2006 | Edgar et al. |
| 2006/0063755 A1 | 3/2006 | Edgar et al. |
| 2006/0063928 A1 | 3/2006 | Edgar et al. |
| 2006/0079858 A1 | 4/2006 | Miller et al. |
| 2006/0079941 A1 | 4/2006 | Ovsyshcher et al. |
| 2006/0094705 A1 | 5/2006 | Edgar et al. |
| 2006/0111704 A1 | 5/2006 | Brenneman et al. |
| 2006/0122666 A1 | 6/2006 | Nghiem et al. |
| 2006/0122863 A1 | 6/2006 | Gottesman et al. |
| 2006/0129050 A1 | 6/2006 | Martinson et al. |
| 2006/0129225 A1 | 6/2006 | Kopia et al. |
| 2006/0142819 A1 | 6/2006 | Penner et al. |
| 2006/0149218 A1 | 7/2006 | Slater et al. |
| 2006/0149339 A1 | 7/2006 | Burnes et al. |
| 2006/0173406 A1 | 8/2006 | Hayes et al. |
| 2006/0173444 A1 | 8/2006 | Choy et al. |
| 2006/0184092 A1 | 8/2006 | Atanasoska et al. |
| 2006/0184154 A1 | 8/2006 | Moberg et al. |
| 2006/0188575 A1 | 8/2006 | Thor et al. |
| 2006/0247311 A1 | 11/2006 | Fraser et al. |
| 2006/0253085 A1 | 11/2006 | Geismar et al. |
| 2006/0264509 A1 | 11/2006 | Fraser et al. |
| 2006/0264894 A1 | 11/2006 | Moberg et al. |
| 2006/0270968 A1 | 11/2006 | Greenberg et al. |
| 2006/0271020 A1 | 11/2006 | Huang et al. |
| 2006/0271112 A1 | 11/2006 | Martinson et al. |
| 2006/0272652 A1 | 12/2006 | Stocker et al. |
| 2006/0276542 A1 | 12/2006 | Fraser et al. |
| 2006/0293309 A1 | 12/2006 | Thor et al. |
| 2007/0003549 A1 | 1/2007 | Ignatovich et al. |
| 2007/0004752 A1 | 1/2007 | Coughlin et al. |
| 2007/0009956 A1 | 1/2007 | Srinivas et al. |
| 2007/0016163 A1 | 1/2007 | Santini et al. |
| 2007/0016170 A1 | 1/2007 | Kovelman |
| 2007/0026042 A1 | 2/2007 | Narayanan |
| 2007/0030764 A1 | 2/2007 | Skyggebjerg et al. |
| 2007/0033074 A1 | 2/2007 | Nitzan et al. |
| 2007/0038100 A1 | 2/2007 | Nita |
| 2007/0040449 A1 | 2/2007 | Spurlin et al. |
| 2007/0048350 A1 | 3/2007 | Falotico et al. |
| 2007/0051362 A1 | 3/2007 | Sullivan et al. |
| 2007/0053996 A1 | 3/2007 | Boyden et al. |
| 2007/0054319 A1 | 3/2007 | Boyden et al. |
| 2007/0054871 A1 | 3/2007 | Pastore et al. |
| 2007/0060652 A1 | 3/2007 | Fraser et al. |
| 2007/0060864 A1 | 3/2007 | Redding |
| 2007/0060871 A1 | 3/2007 | Istoc et al. |
| 2007/0083258 A1 | 4/2007 | Falotico et al. |
| 2007/0087315 A1 | 4/2007 | Stuart et al. |
| 2007/0088248 A1 | 4/2007 | Glenn et al. |
| 2007/0093752 A1 | 4/2007 | Zhao et al. |
| 2007/0098753 A1 | 5/2007 | Falotico et al. |
| 2007/0112298 A1 | 5/2007 | Mueller et al. |
| 2007/0219480 A1* | 9/2007 | Kamen et al. .................. 604/20 |
| 2008/0023593 A1 | 1/2008 | Ritota et al. |
| 2008/0200897 A1 | 8/2008 | Hoss et al. |
| 2008/0281297 A1 | 11/2008 | Pesach et al. |
| 2010/0057003 A1 | 3/2010 | Dos Santos |
| 2010/0106088 A1 | 4/2010 | Yodfat et al. |
| 2010/0152644 A1 | 6/2010 | Pesach et al. |
| 2010/0174225 A1 | 7/2010 | Pesach et al. |
| 2010/0286467 A1 | 11/2010 | Pesach et al. |
| 2010/0292557 A1 | 11/2010 | Pesach et al. |
| 2010/0318035 A1 | 12/2010 | Edwards et al. |
| 2011/0184342 A1 | 7/2011 | Pesach et al. |
| 2011/0288527 A1 | 11/2011 | Pesach et al. |

FOREIGN PATENT DOCUMENTS

| | | |
|---|---|---|
| EP | 1752174 A1 | 2/2007 |
| FR | 2795629 A1 | 1/2001 |
| WO | WO-00/18339 A1 | 4/2000 |
| WO | WO-00/23132 A1 | 4/2000 |
| WO | WO-00/32259 A2 | 6/2000 |
| WO | WO-00/74763 A2 | 12/2000 |
| WO | WO-00/78212 A1 | 12/2000 |
| WO | WO-01/01852 A1 | 1/2001 |
| WO | WO-01/47408 A1 | 7/2001 |
| WO | WO-01/93931 A1 | 12/2001 |
| WO | WO-02/068028 | 9/2002 |
| WO | WO-03/055384 A1 | 7/2003 |
| WO | WO-03/086534 A1 | 10/2003 |
| WO | WO-2006/049570 A2 | 5/2006 |
| WO | WO-2006/084464 A1 | 8/2006 |
| WO | WO-2006/091650 A2 | 8/2006 |
| WO | WO-2008/051924 A2 | 5/2008 |
| WO | WO-2008/114218 A2 | 9/2008 |
| WO | WO-2008/114220 A2 | 9/2008 |
| WO | WO-2008/114223 A1 | 9/2008 |
| WO | WO-2008/114224 A2 | 9/2008 |
| WO | WO-2009/081262 A1 | 7/2009 |
| WO | WO-2010/052579 A2 | 5/2010 |

OTHER PUBLICATIONS

Bos et al., Biomaterials (2005), 26:3901-3909.
Clarke et. al., (2005), Diabetes Care, 28:2412-2417.
Facchinetti et. al., (2007), Journal of Diabetes Science and Technology, 1:617-623.
Heinemann, (2002), Diabetes Technology & Therapeutics, 5:673-682.
Koivisto et al. (1980), British Medical Journal, 280:1411-1413.
Koivisto et al., (1978), The New England Journal of Medicine, 298:79-83.
Magerl et. al., (1996), Journal of Physiology, 497:837-848.
Midttun et. al., (1996), Clinical Physiology, 16:259-274.
Rebrin et al., (2000), Diabetes Technology and Therapeutics, 2:461-472.
Shumaker et al., (2006), Lasers in Surgery and Medicine, 38:211-217.
Sindelka et al., (1994), Diabetologia, 37:377-380.
European Search Report for EP1315647 mailed Jul. 26, 2013.

* cited by examiner

METHOD AND DEVICE FOR DRUG DELIVERY

CROSS-REFERENCE TO RELATED APPLICATIONS

The present application is a continuation patent application and claims priority to U.S. patent application Ser. No. 12/809,425, filed on Mar. 18, 2011, which claims priority to International Patent Application No. PCT/IB2008/003547, to Benny Pesach et al., filed Dec. 18, 2008, and entitled "DRUG DELIVERY DEVICE WITH SENSOR FOR CLOSED-LOOP OPERATION", which claims priority to U.S. Provisional Patent Application No. 61/008,276, filed Dec. 18, 2007, entitled "Method and Device for Drug Delivery", and incorporates their disclosures herein by reference in their entireties.

The present application relates to U.S. Provisional Patent Application Ser. No. 60/895,518, filed Mar. 19, 2007, U.S. Provisional Patent Application Ser. No. 60/895,519, filed Mar. 19, 2007, U.S. Provisional Patent Application Ser. No. 60/912,698, filed Apr. 19, 2007, U.S. Provisional Patent Application Ser. No. 60/940,721, filed May 30, 2007, U.S. Utility patent application Ser. No. 11/821,230, filed Jun. 21, 2007, U.S. Provisional Patent Application Ser. No. 61/008,278, filed Dec. 18, 2007, U.S. Provisional Patent Application Ser. No. 60/956,700, filed Aug. 19, 2007, U.S. Provisional Patent Application Ser. No. 60/970,997, filed Sep. 10, 2007, U.S. Provisional Patent Application Ser. No. 61/008,325, filed Dec. 18, 2007, U.S. Provisional Patent Application Ser. No. 61/008,274, filed Dec. 18, 2007, U.S. Provisional Patent Application No. 61/008,277, filed Dec. 18, 2007, and International Patent Application No. PCT/IB2008/051044, filed Mar. 19, 2008. Each of the foregoing disclosures is incorporated by reference herein in its entirely.

BACKGROUND OF THE INVENTION

1. Field of the Invention

The present invention relates to systems and methods for delivering drugs to a patient. In particular, the present invention relates to systems and methods for more efficient and controlled subcutaneous infusion of drugs or substances.

2. Background

Diabetes is a very serious illness affecting millions of people today. Many diabetic patients require injection of insulin to maintain proper levels of glucose in their blood in order to survive. Such injections of insulin are done using various drug delivery systems.

Many medical treatment systems and methods involve drug delivery systems that employ subcutaneous infusions of therapeutic fluids, drugs, proteins, and other compounds. Such delivery systems and methods, especially in the area of insulin delivery, have made use of subcutaneous catheters and continuous subcutaneous insulin infusion ("CSII") pumps. In conventional insulin pumps, the pump can be attached to a disposable thin plastic tube or a catheter through which insulin passes into the tissue. The catheter can be inserted transcutaneously, typically through the skin of the patient's abdomen, and is changed every two to three days. New types of insulin pumps, such as the OmniPod pump manufactured by Insulet Corporation, do not have an external catheter and, instead, a catheter port is embedded into the pump mechanism.

In many instances, patients require insulin delivery around the clock to keep proper levels of glucose in their blood. Insulin can be delivered at a basal rate or in bolus doses. The basal rate represents insulin that is continuously delivered to the patient. Such a continuous delivery of insulin keeps the blood glucose level in the desired range between meals and overnight. The bolus dose is an amount of insulin delivered to the patient according to food intake at meals, particularly carbohydrates. When patient consumes food, his or her levels of glucose rise. Some conventional pump mechanisms are configured to react upon command, or by way of an automated procedure, to the increase in glucose levels by delivering a bolus dose of insulin that matches the rise in the level of glucose and prevents large fluctuations in glucose levels. However, this attempt at control is confounded by the fact that there is usually a variable profile of the absorption of insulin from the injection site to the blood circulation. This variability of the insulin absorption results in an error of up to 30% in insulin levels in the blood and hence results in variability of the insulin effect. Such variability in turn causes extreme variability in the resulting glucose levels, which may cause hyperglycemic and hypoglycemic events; in any case such variability itself has been shown to be potentially damaging to organs and body systems. (See, e.g., Lutz Heinemann, "Variability of Insulin Absorption and Insulin Action", Diabetes Technology & Therapeutics, Vol. 4 No 5, 2002).

SUMMARY OF THE INVENTION

In some embodiments, the present invention relates to a system and a method having a more consistent and lower variability of the amount and profile of an absorbed delivered drug into the circular blood and lymph system when administered invasively. In some embodiments, the present invention relates to a system and method for invasive administration through an infusion pump. Some embodiments of the present invention relate to a system and method for administering a drug which affects and/or controls blood sugar for preventing and/or reducing occurrence of hyperglycemic and hypoglycemic events in a subject.

The systems, apparatuses, methods and devices described herein overcome the drawbacks described in the background art by providing a system, device and method for at least reducing the variability of absorption of a drug to a subject when administered invasively. As used in the following specification, "invasively" means any type of administration, which induces at least a temporary breach in the skin of the subject, including any type of parenteral administration, which, for example, may include, but is not limited to, an intravenous administration or any type of injection or infusion whether subcutaneous, intradermal, transdermal, intramuscular, intraperitoneal, intrathecal and the like. For the non-limiting, illustrative purposes and ease of the following description only, the below described embodiments relate to administration of a drug using a pump, for example, an infusion pump, as described herein. In some embodiments, the infusion pump can be connected to the subject on a continuous basis. As can be understood by one skilled in the art, the infusion pump can be connected to the patient subject in any other desired way. Some embodiments of the present application can be used with transdermal drug delivery as well, although some types of transdermal drug administration can be used for temporarily breaching the skin of the subject.

Again for the purposes of illustration and without any intention of being limiting, the exemplary drug discussed herein can be a drug for affecting and/or controlling blood sugar, for example, insulin. As can be understood by one skilled in the art, other types of drugs and/or compounds can be used with the present invention. As stated above, insulin absorption is generally highly variable. Even with the use of a pump to provide a more rapid response to measured and/or anticipated changes in blood glucose levels, subjects may still experience variable blood glucose levels due to the variability of effective insulin in the body. In some embodiments, the methods, devices and systems of the present invention solve the deficiencies of the conventional systems by overcoming the drawbacks associated with insulin administration and/or absorption.

One source for the variability of the insulin absorption in the subcutaneous tissue, among other physiological parameters, is the variation in the local blood perfusion at the insulin infusion site. Another source for variability is the variation in the capillary wall's permeability. These physiological parameters are influenced by temporal physical activity or exercise, ambient temperature, or any other factors. Also, the physiological parameters correlate with the skin temperature. Other types of potentially variable characteristics, relating to the subject and/or the subject's environment, may also affect drug efficacy during invasive drug administration.

In some embodiments, the methods, devices and systems of the present invention relate to a drug delivery device capable of adjusting administration of a drug to a patient by performing various measurements relating to a patient, wherein at least one of the measurements is different from a measurement of a particular drug level in the blood of the patient. The measurements are then used to adjust administration of a drug in order to improve its effects (e.g., regulation of glucose levels in cases of insulin delivery). The measurements can include physiological, biochemical, environmental or any other measurements. Non-limiting examples of physiological measurements include skin temperature measurements; biochemical measurements include blood insulin level and/or the rate of change of blood insulin level measurements after administration of insulin; and, environmental measurements include ambient (e.g., air) temperature measurements.

According to some embodiments, a drug delivery device can be combined with at least one sensor for measuring parameters that can influence drug's pharmacokinetics and/or pharmacodynamics, including, for example, skin temperature, ambient temperature, physical activity, local blood perfusion at the drug infused tissue region, and/or others. As can be understood by one skilled in the art, the present invention can include one or more additional sensors that measure the above and any other parameters that can influence drug's pharmacokinetics and/or pharmacodynamics. In some embodiments, the measured parameters can be used by a controller to calculate an adjustment to the delivered drug dose or rate in order to improve the accuracy and/or the repeatability of the desired effect of the delivered drug.

For example, with regard to insulin, the controller can use the measurement information to calculate an adjustment to the delivered insulin dose or rate or delivery profile in order to improve accuracy or repeatability of the insulin effect. In some embodiments, the information can be used to reduce glucose variations during a particular time (e.g., a day). The information can be also be used in determination of postprandial glucose levels. In some embodiments, one or more sensors can be disposed at the insulin pump for insulin infusion.

Past studies, such as those performed by Koivisto checked the influence of the ambient temperature or the skin temperature on insulin absorption. (See, e.g., Koivisto, V.A., "Sauna-Induced acceleration in Insulin Absorption from Subcutaneous Injection Site", British Medical Journal, Vol. 280, 1980). Koivisto checked the effect of placing the subject in a sauna (twice for 25 minutes at 85° C.), in order to heat the skin, on the disappearance rate of 125I-labelled rapid acting insulin. The result was the observation of 110% faster absorption when the subject was in the sauna as compared with room temperature ($p<0.01$). Also, in the study, the postprandial glucose rise 2 hours after breakfast was reduced to 3.2 mmol/l instead of 5 mmol/l postprandial glucose rise at room temperature. Other studies, such as Sindeka et al., showed a positive correlation ($p<0.0008$) between local skin temperature at the insulin injection site in the range of 30° C.-37° C. and the serum insulin level 45 minutes after injection of the insulin. (See, e.g., Sindeka, G., et al., "Effect of Insulin Concentration, Subcutaneous Fat Thickness and Skin Temperature on Subcutaneous Insulin Absorption in Healthy Subjects", Diabetologia, Vol. 37 No. 4, 1994).

As indicated by the studies, the ambient and skin temperatures influence on the insulin absorption in the blood. Thus, by measuring the skin and/or ambient temperatures, the delivered insulin dose or delivery profile can be adjusted. However, in the conventional systems, the above observation is not practically useful for increasing efficacy of insulin administration, because the observation alone is not sufficient. Thus, there is a need for a method and a system that would adjust one or more aspects of insulin administration based on the observed temperature.

According to some embodiments, the present invention relates to a drug delivery apparatus and/or device including a sensor that measures the skin temperature and/or the ambient temperature. The sensor can be connected using a wire or wirelessly to a processing unit that can use the measured temperature to calculate an adjustment to an insulin dose or delivery profile. The adjustment can include a change in the amount of insulin delivered and/or timing of delivery and/or rate of delivery. The timing of delivery can also relate to the frequency of delivery for a plurality of insulin doses. The insulin adjustment can also be applied to a basal insulin level for a certain period and/or to a bolus insulin profile for a certain period, according to the insulin levels being delivered at that time. Information regarding the insulin adjustment is preferably transmitted either through wire(s) or wirelessly to an insulin pump that applies the adjusted insulin level and determines an insulin administration profile according to the calculated adjustments.

In some embodiments, the present invention relates to a device that includes a user interface, whether as part of the device and/or as part of an external device, for displaying information about the insulin adjustment. The user interface may be any type of screen or other visual display, and/or an audio display and/or a tactile display. The user interface may be provided through an external device, including but not limited to, a computer, a cellular telephone, a pager, a PDA, an interactive television or any other suitable device. The user interface may be used by the subject, such as a patient, a physician, a medical professional, and/or other individual(s). In some embodiments, the adjustment can be displayed before it is applied to the patient. In some embodiments, the user of the interface can be asked to confirm the insulin level adjustment beforehand.

In some embodiments, the present invention relates to an apparatus for controlling administration of a drug to a body of a patient. The apparatus includes a drug infusion device configured to deliver drug at a predetermined location in the body of the patient, at least one sensor disposed in the drug infusion device and configured to measure a corresponding property related to the patient and selected from the group consisting of physiological properties, biochemical properties, environmental properties and drug-related properties, a controller disposed in the drug infusion device and configured to receive from the at least one sensor data representative of the measured corresponding property and based on the received data, determine a drug delivery rate. The drug delivery device is configured to deliver the drug to the body of the patient based on the determined drug delivery rate.

In some embodiments, the present invention relates to a method for controlling administration of a drug to a body of a patient using a drug delivery device having at least one sensor. The method includes using the at least one sensor, measuring a corresponding property related to the patient and selected from the group consisting of physiological properties, biochemical properties, environmental properties and drug-related properties. The method further includes receiving, from the at least one sensor, data representative of the measured corresponding property, then based on the received data, determining a drug delivery rate, and, using the determined drug delivery rate, delivering the drug to the body of the patient at a predetermined location on the body of the patient.

In some embodiments, the present invention relates to a system for managing administration of a drug. The system includes a device for administering the drug to a subject, a sensor for detecting at least one parameter selected from the group consisting of: physiological, biochemical, environmental, and a parameter related to the drug itself, and a controller for controlling the device for administering the drug according to the at least one parameter.

In some embodiments, the present invention relates to a drug administration device for administering a drug to a subject. The device includes a sensor for detecting at least one parameter selected from the group consisting of: physiological, biochemical, environmental, and a parameter related to the drug itself, and a controller for controlling administration of the drug according to the at least one parameter.

In some embodiments, the present invention relates to a method for managing administration of a drug to a subject. The method includes measuring at least one parameter selected from the group consisting of: physiological, biochemical, environmental, and a parameter related to the drug itself, and adjusting at least one aspect of administration of the drug according to the at least one parameter.

The term "drug", as used herein, is defined to include any pharmaceutically active compound including but not limited to compounds that treat diseases, injuries, undesirable symptoms, and improve or maintain health.

Unless otherwise defined, all technical and scientific terms used herein have the same meaning as commonly understood by one of ordinary skill in the art to which the disclosure pertains. The materials, methods, apparatuses, systems, devices and examples described herein are illustrative only and not intended to be limiting.

Although the foregoing has been described with respect to drug delivery of insulin for the treatment of diabetes, this is a non limiting example of the present disclosure. Any additional chronic or acute condition may be treated with the drug delivery device of the present invention, for example including but not limited to hypoxia, anemia, cholesterol, stroke, heart or the like.

Implementation of the methods and apparatus of the present disclosure involves performing or completing certain selected tasks or steps manually, automatically, or a combination thereof. Moreover, according to actual instrumentation and equipment of some of the embodiments of the methods and apparatuses of the present disclosure, several selected steps could be implemented by hardware or by software on any operating system of any firmware or a combination thereof. For example, as hardware, selected operations of the methods, apparatuses, systems and devices described herein could be implemented as a chip or a circuit. As software, selected operations could be implemented as a plurality of software instructions being executed by a computer using any suitable operating system. In any case, selected operations of the method and system of the present disclosure could be described as being performed by a data processor, such as a computing platform for executing a plurality of instructions.

Although the present disclosure is described in relation to a "computer" or a "computer network", it should be noted that any device featuring a data processor and/or the ability to execute one or more instructions may be described as a computer, including but not limited to a PC ("personal computer"), a server, a minicomputer, a cellular telephone, a smart phone, a PDA ("personal data assistant"), a pager. Any two or more of such devices in communication with each other, and/or any computer in communication with any other computer, may comprise a "computer network".

BRIEF DESCRIPTION OF THE DRAWINGS

The disclosure is herein described, by way of example only, with reference to the accompanying drawings. With specific reference now to the drawings in detail, it is stressed that the particulars shown are by way of example and for purposes of illustrative discussion of the embodiments of the present disclosure only, and are presented in order to provide what is believed to be the most useful and readily understood description of the principles and conceptual aspects of the methods, apparatuses, systems and devices described herein. In this regard, the description taken with the drawings makes it apparent to those skilled in the art how the several forms of the disclosure may be embodied in practice.

In the above figures, like reference numbers and designations indicate similar elements.

DETAILED DESCRIPTION OF THE INVENTION

In some embodiments, the present invention relates to a drug delivery device, apparatus, system and method for controlling efficacy of invasive administration of a drug by performing one or more measurements relating to the subject (e.g., patient). The measurements include, but are not limited to, measurements that are other than measurements of a level of the drug in the blood. The measured information is then used to calculate an adjustment to administration of a drug to improve effects of the drug (e.g., improvement of regulation of glucose levels in cases of insulin delivery), Information regarding level of the drug in the blood may be combined with one or more subject's measurements to determine what the adjustment should be. In some embodiments, the measurements can include one or more of the following: a physiological, a biochemical, an environmental and/or any other type of measurement. Non-limiting examples of physiological measurements include skin temperature, blood flow and blood volume at the site of administration, and others. Non-limiting examples of biochemical measurements include blood insulin level and/or the rate of change of blood insulin levels after administration of insulin. As can be understood by one skilled in the art, insulin can be substituted for any other type of drug. Non-limiting examples of an environmental measurement include ambient (e.g., air) temperature.

In some embodiments, the present invention includes a sensor for measuring at least one of the ambient and/or subject skin temperature(s). A plurality of sensors can be used to measure the ambient temperature and also the skin temperature. A sensor can be provided to measure the level of the drug in a body tissue, which can include a body fluid. In some embodiments, the sensor can be configured to measure (directly or indirectly) the level of the drug in the blood. In some embodiments, the sensor can also measure the rate of change of the drug level after administration thereof.

In some embodiments, part or all of the described components are disposed in a single housing. For instance, the processing unit can be disposed in the insulin pump housing. In some embodiments, the above-described calculation can be performed by the insulin pump's processing unit. In some embodiments, the skin and/or ambient temperature sensors, the processing unit and the insulin pump can be disposed in a single housing. The insulin pump housing can also include a display that can be configured to show the adjusted insulin level. The display can be configured to be a part of PDA, a computer, a cellular phone, or any other suitable device. In some embodiments, the skin temperature is measured using a temperature sensor that can be configured to be attached to the skin.

The principles and operation of the present invention can be better understood with reference to the drawings and the accompanying description.

Figure 1:
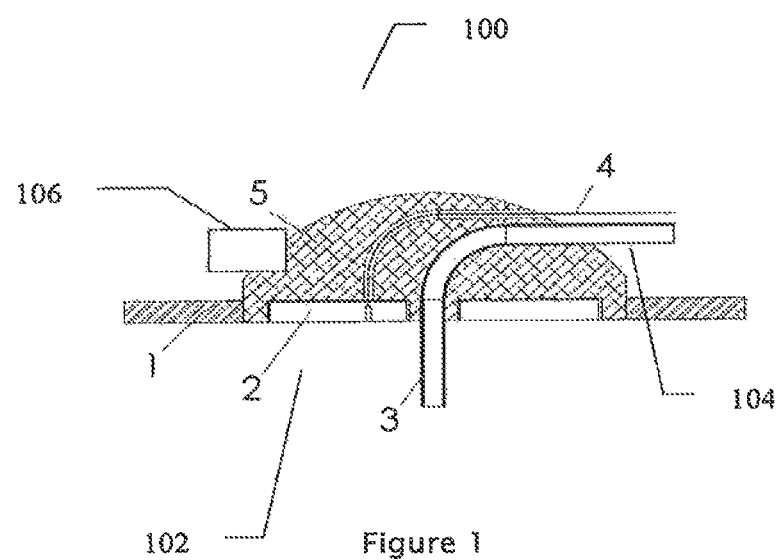
FIG. 1 schematically illustrates an exemplary catheter for drug delivery with a temperature sensor for measurement of the skin temperature, according to some embodiments of the present invention.

FIG. 1 illustrates an exemplary insulin infusion device 100, according to some embodiments of the present invention. As can be understood by one skilled in the art, the device 100 is drawn to a non-limiting embodiment of an insulin infusion device. For illustrative, non-limiting purposes only, the following description will be presented referencing "an insulin infusion device". As can be understood by one skilled in the art, device 100 can be any drug infusion device and its associated elements can be configured to perform appropriate functions associated with such drug infusion device in accordance with the embodiments of the present invention.

The device 100 includes a securing element 5 for securing a drug (e.g., insulin) infusion set coupled to the skin of a patient using a skin adhesive 1, a catheter 3 for insertion into a subcutaneous compartment of the patient and coupled to a catheter tube 104 protruding outside of the securing element 5, at least one sensor 102, and an ambient temperature sensor 106. The sensor 102 can include but is not limited to a skin temperature sensor 2. As shown in FIG. 1, the device 100 can include two sensors 102. As can be understood by one skilled in the art, there can be more than one sensor 102 associated with the device 100. In some embodiments, the skin temperature sensor 2 is disposed in the insulin infusion set securing element 5 such that the skin temperature sensor 2 measures the temperature of the skin adjacent to the tissue region which is configured to receive the drug (not shown in FIG. 1). In some embodiments, the insulin is infused through the catheter 3 into the tissue disposed underneath the skin of the patient. The insulin infusion set securing element 5 is attached to the skin with adhesive 1, such that the temperature sensor 2 is in direct contact with the skin with or without any additional matching hydrogel or another coupling material (not shown in FIG. 1).

As illustrated in FIG. 1, the temperature sensor 2 is configured to be coupled to an insulin pump (not shown in FIG. 1) using a wire 4. In some embodiments, the wire 4 can be attached to the catheter tube 104, embedded in the tube 104 and/or otherwise connected to or combined with tube 104. In some embodiments, the device 100 can be configured to include a an optional catheter connector (not shown in FIG. 1) for attaching and detaching the tube 104 to and from a portion of the catheter 3 that is inserted into the body of the patient (not shown in FIG. 1). The optional catheter connector can be also configured to connect and disconnect the wire 4. The optional catheter connector can be configured to allow easy coupling and de-coupling of the device 100 from the skin of the patient. In some embodiments, the skin temperature sensor 2 can be configured as a separate unit adhered to the skin proximate to the insulin infusion set securing element 5.

In some embodiments, the device 100 can be configured to include an ambient temperature sensor 106 for measuring a temperature of the environment at or proximate to the skin of the patient. The ambient temperature sensor 106 can be configured to measure, for example, the temperature of air surrounding the device 100. As can be understood by one skilled in the art, the sensor 106 can be configured to measure other parameters besides the ambient temperature.

Figure 2:
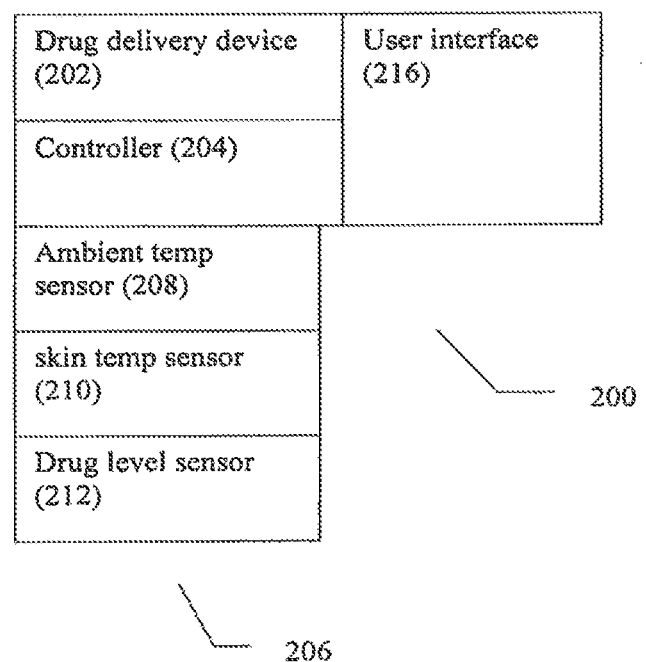
FIG. 2 is a block diagram of an exemplary system including a drug delivery device and a controller, according to some embodiments of the present invention.

In some embodiments, the ambient temperature sensor 106 can be disposed in the housing of the drug infusion set, as illustrated in FIG. 1. As shown, the ambient temperature sensor 106 is attached and/or embedded or otherwise combined with the securing element 5. In some embodiments, the sensor 106 can be disposed on the upper side of securing element 5, such that the ambient temperature sensor 106 can be configured to be exposed to the surrounding air for the measurement of the surrounding air temperature. In some embodiments, the ambient temperature sensor 106 can be coupled to the drug delivery device (e.g., an insulin pump, as shown in FIG. 2), and/or to a third party unit, such as, a PDA, a computer, a laptop, a cellular telephone, or any other external computer or other suitable device. The sensor 106 can be coupled to these devices via a wired, wireless, wireline, RF, or any other type of suitable connection. In some embodiments, the ambient temperature sensor 106 is disposed in the drug delivery device and connected to its processing unit, as shown in FIG. 2. In some embodiments, the ambient temperature sensor 106 is disposed in an external unit, such as, a PDA, a personal computer, a laptop, a cellular phone, or any other suitable device.

Referring to FIG. 2, an exemplary system 200 having a drug delivery device 202 and a controller 204 is shown. In some embodiments, the controller 204 can be combined with the drug delivery device 202. Alternatively, the controller 204 can be configured to be separate from the drug delivery device 202. The latter implementation is shown for the purpose of illustration only. The controller 204 is configured to control the administration of the drug (e.g., insulin) through the drug delivery device 202 by, for example, activating and/or deactivating drug delivery device 202, or by otherwise enabling or blocking administration of drug by the drug delivery device 202.

In some embodiments, the system 200 includes at least one sensor 206. In alternate embodiments, the system 200 can be configured to include a plurality of sensors 206. The multiple sensors 206 can be configured to include an ambient temperature sensor 208, a skin temperature sensor 210, and/or any other sensors. The temperature information obtained from the sensor 206 can be communicated to the controller 204. Based on the communicated information, the controller 204 can be configured to adjust at least one aspect of drug administration by the drug delivery device 202 to the patient. Such aspects can include, but are not limited to, timing(s) of dose(s), dose(s) amount(s), rate(s) of administration of a single dose, temporal profile of the dose and/or timing of administration of a plurality of doses. Such an adjustment may be made, for example, according to a procedure depicted in FIG. 3. For example, in some embodiments, if the skin temperature is relatively high, the controller 204 can be configured to reduce the amount of insulin to be administered to the patient in at least one dose, since higher skin temperature tends to lead to an increased bioavailability the dose of insulin. In another example, the controller 204 can be configured to fit the insulin delivery profile of an insulin pump and to optimize the insulin profile in the blood in order to obtain the smallest postprandial glucose excursion with smallest chance of postmeal hypoglycemia. Such improved profile can be, for instance, used to reduce the amount of an infused insulin in the first hour, when insulin absorption is accelerated, and increase it after an hour. In some embodiments, another option is to apply a split bolus with a reduced first bolus and an increased second bolus. In some embodiments, another exemplary profile use the advantage of the accelerated insulin absorption, when the local temperature is elevated, to keep the infusion rate at the first hour the same and only to slightly increase the delivery rate afterwards at after the first to second hour to compensate for the faster clearance of the insulin infusion site without getting into hypoglycemia. Other adjustments of the insulin delivery profile are possible and may depend also in the meal composition, injection site and other measured parameters as discussed in the present application. For instance, in case of carbohydrate rich meal, where the glucose is proposed to rise more rapidly, it may be advantageous to have enhancement of the insulin absorption at the first hour and in this case down adjustment of the insulin dose at the first hour will not be applied. On the other hand, in case of fat rich meal or low carbohydrate meal, where the glucose is proposed to rise more slowly, it may be advantageous to further reduce the blood insulin level at the first hour and increase it later on, so in this case if the skin temperature is elevated down adjustment of the insulin dose at the first hour will be applied. Different drugs may have different adjustments made, since the effect of temperature on these drugs may vary.

The sensors 206 may also include a drug level sensor 212 for measuring the level of drug in a tissue of the subject, such tissue including, but not limited to, one or more of blood or skin. The information from the drug level sensor 212 is transferred to the controller 204 to adjust the dose accordingly. The drug level information may be used with the temperature information to control drug delivery to the subject.

The system 200 further includes a user interface 216 in communication with the controller 204 to enable the user (or any another individual) to view information regarding the administration of the drug. Such information can include information about a dose being administered, one or more of drug levels, drug pharmacokinetics, skin temperature, administration characteristics, drug absorption process components such as drug disassociation process, diffusion and absorption into the blood, lymph, cells, etc., as well as any other parameters, factors, and/or characteristics. Additionally, the user interface is configured to enable control of one or more aspects of the drug administration. For example, the user can input data to enable control of the quantity of the administered drug, timing, rate of administration of a single dose of the drug, timing of administration of a plurality of doses of the drug, etc. If more than one drug or types of drug are administered through the system 200, then the user interface 216 can be configured to enable the user to provide information about the drug being administered. Such control can be accomplished through use of a pull down menu, text entry box, and/or any other type of information entry mechanism.

In some embodiments, the controller 204 can be configured to identify one or more alert and/or alarm conditions related to the temperature by identifying a non-realistic (e.g., rapid changes of skin temperature, or the temperature is too high, too low, or otherwise inconsistent with administration of the drug to the patient) skin temperature. Such non-realistic temperature can occur for example if the skin temperature sensor is fully or partially detached from the skin of the patient. Based on such identification, the controller can be configured to take an appropriate remedial action, such as, stopping the drug dose adjustment. In some embodiments, the controller 204 can be configured to initiate an alert to the user, for example, through the user interface 216, which can include a visual display and/or audio means generating a sound, so that the user can be properly alerted and determine the cause of the identified temperature problem. In some embodiments, the user, upon discovering the cause of the alert/alarm, can nevertheless continue with the drug dosage adjustment process.

In the embodiments when an insulin pump and/or infusion sets are used, the controller 204 can be configured to use the skin temperature sensor variations to alert the user to possible disconnection or leakage of insulin from the infusion set. Such disconnection or leakage can lead to hyperglycemia events, and thus, the user should be timely alerted to these conditions.

Figure 3:
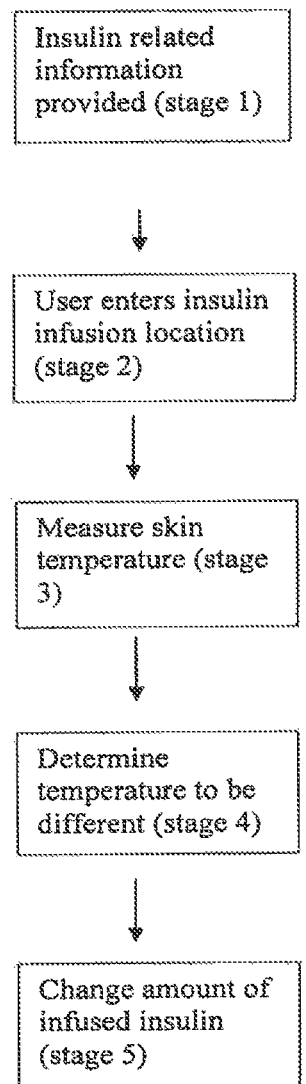
FIG. 3 is a flow chart of an exemplary procedure for adjusting a drug delivery dosage (e.g., insulin), according to some embodiments of the present invention.

FIG. 3 is a flow chart illustrating an exemplary procedure 300 for adjusting an insulin dose or delivery profile or some other drug dosage level, according to some embodiments of the present invention. As can be understood by one skilled in the art, the procedure 300 is applicable to any type of drug administration and is not limited to insulin. In stage 1, insulin information, such as insulin concentration or type is provided. At this stage, a basal amount of insulin for the user can also be provided. In stage 2, the insulin injection location on the body of the patient is determined. In stage 3, the temperature of the skin of the patient is measured. In stage 4, the procedure 300 determines whether the skin temperature is different from what is considered to be "normal" or regular temperature level. In stage 5, based at least in part on the determination of whether the measured temperature is different from the "normal" temperature the amount of infused insulin can be changed. In some embodiments, if the skin temperature is determined to be higher than the "regular" or normal skin temperature, the amount of infused insulin can be reduced because the delivered insulin can be absorbed by the body at a higher rate, i.e., higher than the rate of absorption at the "regular" temperature, and also because the bioavailability of the delivered insulin is higher. Generally, the relationships between skin temperature and Serum Insulin ("SI")

level 45 min after injection of insulin bolus and the temperature (T) at temperature range of 30-37° C. have been determined to be as follows:

$$SI[\text{pmol/l}]=3.05*T[°\text{ C.}]-73.8 \text{ for } U40 \text{ insulin; and}$$

$$SI[\text{pmol/l}]=2.12*T[°\text{ C.}]-48.7 \text{ for } U100 \text{ insulin.}$$

Thus, for example, a possible adjustment for the insulin dose for U40 insulin is given by:

Adjusted Insulin Dose=Regular Insulin Dose*Adjustment Factor where $$\text{Adjustment Factor}=(3.05*T_{Regular}[°\text{ C.}]-73.8)/(3.05*T[°\text{ C.}]-73.8)$$

where $T_{Regular}$ is the "regular" skin temperature for which the regular insulin dose is calculated and T is the current skin temperature in the temperature range of 30-37° C., as measured by the skin temperature sensor. For larger temperature range, a more complex expression may be used and applied.

In some embodiments, in stage 1, the user enters the insulin concentration through a user interface (for example, the user interface disposed on the insulin pump) such that the best expression for a specific insulin concentration can be used in the calculation of the dose adjustment. In some embodiments, in stage 2, using the user interface, the user can enter the location of the insulin infusion site such that the best expression for a specific infusion site can be used in the calculation of the dose adjustment. In some embodiments, other expressions may be used, including, for example, non-linear adjustment expressions that provide the best correction to the infused insulin dose.

In some embodiments, the insulin dose or delivery profile can be adjusted if the skin temperature is determined to be higher than a previously determined "normal" skin temperature. In some embodiments, the insulin dose or delivery profile can be adjusted if the skin temperature is determined to be lower than a previously determined "normal" skin temperature. In some embodiments, both types of adjustments can be performed. In either case, an adjustment can be performed if the degree of difference is above a predetermined temperature threshold.

Figure 8:
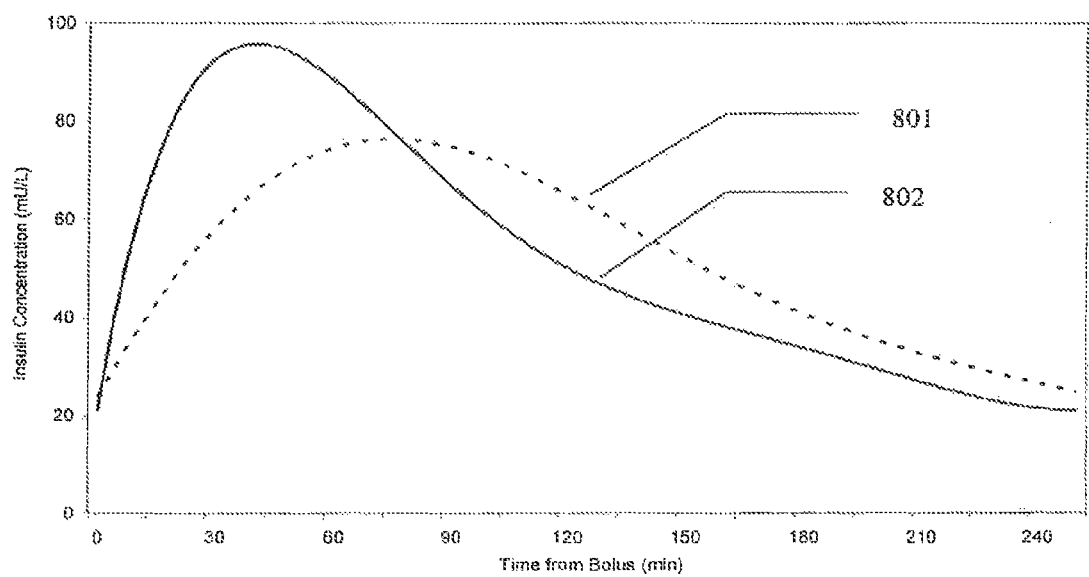
FIG. 8 is a plot illustrating an effect of skin temperature in the insulin pharmacokinetics, according to some embodiments of the present invention.

In some embodiments, the insulin dose adjustment can be time-dependent and also relates to the time passed from the insulin bolus delivery or the particular time of day at which the procedure is to be performed. FIG. 8 is an exemplary plot illustrating the effect of a skin temperature on the insulin pharmacokinetics ("PK"). As shown in FIG. 8, the insulin PK was measured in nine subjects who used a rapid acting insulin (0.15 U/kg) with an insulin pump, such as, an insulin pump manufactured by Medtronic Minirned, Inc., Northridge, Calif., USA. The plot illustrates two curves 801 (i.e., a dashed line), which represents subjects having normal skin temperature of approximately 31° C., and 802 (i.e., a solid line), which represents subjects having an elevated skin temperature of approximately 38.5° C. for a period of approximately 30 minutes. The study was crossover study, wherein the subjects (e.g., Type I Diabetic patients) repeated insulin injection together with a standardized meal twice. At one case with normal skin temperature and on the other case with elevated skin temperature. As shown in FIG. 8, curve 802 has a higher insulin PK profile at the initial 80 min, where the higher temperature induces higher local blood perfusion and faster absorption of the insulin into the blood and lower afterwards. This is caused by the faster clearance of insulin from the injection site. Thus, to optimize the insulin delivery and reduce its variability, the meal insulin bolus can be divided into several time-dispersed boluses, such as a square wave or a split bolus. In some embodiments, each of these can be adjusted based on the prospected insulin absorption profile according to the measured skin temperature and/or local blood perfusion at the injection, and/or other parameters, as discussed in the present application. For instance, by applying a proper temperature correction adjustment factors to the series of time dispersed insulin boluses, the difference between PK profiles in curves 801 and 802 can be reduced.

In some embodiments, alternative and/or additional parameters can be employed for the purposes of dose adjustment calculations. The calculations include parameters pertaining to the measured ambient temperature, for example, by the ambient temperature sensor, the level of physical activity (as discussed below), and/or the level of local blood perfusion (as also discussed below). For any of the above adjustments, the insulin dose adjustment can be applied to the basal insulin level and/or to bolus insulin delivery.

Studies have been performed to examine the effects of exercising on insulin absorption, e.g., Koivisto, V.A., Felig, P., "Effects of leg exercise on insulin absorption in diabetic patients", The New England Journal of Medicine, Vol. 298, 79-83 (1978). Koivisto examined the effect of a leg exercise on insulin absorption from various injection sites using 125I-labelled rapid acting insulin, which was injected subcutaneously into the leg, arm or abdomen of patients with insulin-dependent diabetes before one hour of intermittent leg (bicycle) exercise and on a resting, control day. The study determined that insulin disappearance from the leg was increased by 135 percent during the first 10 minutes of leg exercise and remained 50 percent above resting levels after 60 minutes. On the other hand, leg exercise had no effect on insulin disappearance from the arm. However, insulin disappearance from the abdomen was reduced during the post-exercise recovery period. Thus, it was determined that exercise contributes, and may improve, insulin delivery to the body.

Figure 4:
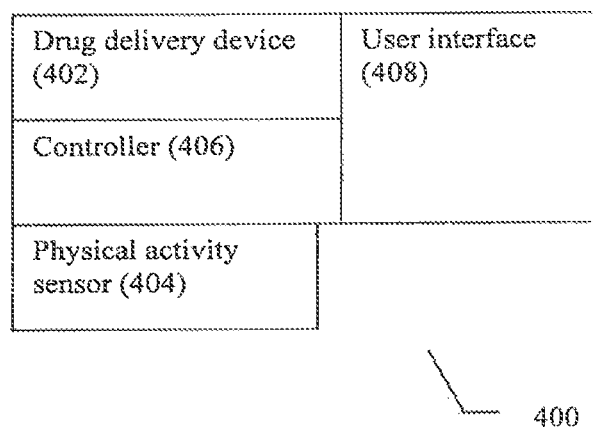
FIG. 4 is a block diagram of another exemplary system that includes a drug delivery device and a sensor for measuring physical activity of a patient, according to some embodiments of the present invention.

FIG. 4 illustrates an exemplary system 400 that includes a drug delivery device 402 with a sensor 404 for measuring a physical activity of the patient, according to some embodiments of the present invention. The sensor 404 can be a pedometer and/or more complicated sensors, such as a SenseWear® WMS sensor, manufactured by BodyMedia Inc. In some embodiments, the sensor 404 can provide real-time displays and continual monitoring of parameters such as calories burned, duration of physical activity, sleep, and other parameters.

In some embodiments, the physical activity sensor 404 can be configured to communicate with a controller 406 via a wired, wireless, wireline, RF, or any other type of suitable communication. The controller 406 uses data communicated by the sensor 404 to compute an adjustment to at least one aspect of administration of therapeutic drugs (e.g., insulin) from the drug delivery device 402. In some embodiments, the aspect can include one or more of the following: timing of a dose, dosage amount, rate of administration of a single dose, temporal profile of the administration of the dose and/or timing of administration of a plurality of doses. In embodiments, where the administered drug is insulin, the insulin adjustment can be applied to a basal insulin level for a certain period and/or to a bolus insulin profile for a certain period, according to the insulin levels delivered at that time. The insulin adjustment value, or the new adjusted insulin level, can be transmitted either via a wired, wireless, wireline, RF, or any other type of communication to the drug delivery device 402. In some embodiments, for example, an insulin pump applies the adjusted insulin level and corrects the delivered insulin levels according to the computed adjustments.

In some embodiments, the insulin adjustment or the new adjusted insulin level is displayed to the patient and/or other relevant individual(s) (e.g., physicians and/or other medical personnel), before the adjustment is applied. In some embodiments, the user interface 408 displays the appropriate insulin levels and can be configured to operate similarly to the user interface 216 shown in FIG. 2. In some embodiments, the user interface 408 can prompt the user to confirm the insulin level adjustment before it is applied to the patient.

In some embodiments, part or all of the described components of the system 400 can be disposed in the same housing (not shown in FIG. 4). For instance, the controller 406 can be disposed in the housing of the drug delivery device 402, wherein the drug delivery device can be an insulin pump. In some embodiments, the adjustment computations described herein can be performed by a processing unit disposed in the insulin pump or some other drug delivery device. In some embodiments, the physical activity sensor 404, the controller 406 and/or the insulin pump (or some other drug delivery device) can be disposed in the same housing. The user interface can be part of a separate device, as previously described, or can be disposed in the housing of the drug delivery device 402.

In some embodiments, the physical activity sensor 404 can be disposed in the insulin infusion set (not shown in FIG. 4). The physical activity sensor 404 can measure the local physical activity at the insulin infusion site in order to adjust the insulin dose or delivery profile being infused into the infusion site based on data measured at that site. An example of implementation of such physical activity sensor 404 is an accelerometer with one (1) to three (3) axes disposed in the securing element of the infusion set.

In some embodiments, when the physical activity level is relatively high, the controller 406 can be configured to reduce the amount of infused insulin because insulin is generally absorbed at a higher rate (at least in some locations in the body) and has a relatively high bioavailability level when the patient is engaged in a physical exercise. For instance, in situations in which a high leg physical activity is measured by the physical activity sensor the insulin infusion rate into the leg may be multiplied by a time variable adjustment factor that equals $1/2.35=0.43$ at 10 minutes of leg exercise and equals $1/1.5=0.67$ at 60 minutes. In some embodiments, where the site of infusion is patient's abdomen, the controller 406 can be configured to increase the amount of infused insulin because infusion at this location, as it was shown, results in a reduced absorption of insulin during exercise.

Figure 5:
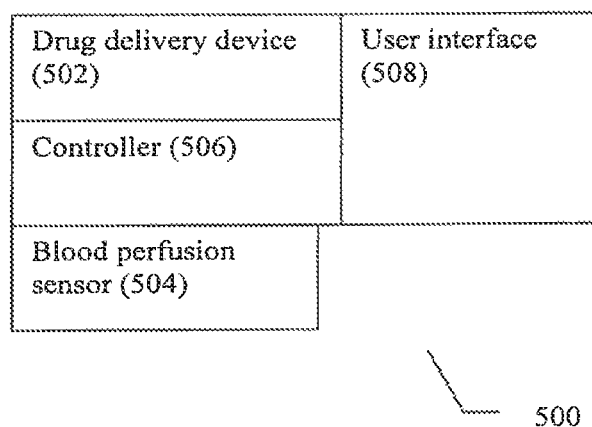
FIG. 5 is a block diagram of another exemplary system that includes a drug delivery device and a sensor for measuring local blood perfusion of a patient at the drug infused tissue region, according to some embodiments of the present invention.

FIG. 5 illustrates another exemplary system 500 having a drug delivery device 502 with a sensor 504 that measures a local blood perfusion at the drug infused tissue region, according to some embodiments of the present invention. The blood level sensor 504 can be configured to include any type of suitable sensor for determining such perfusion, including, for example, a hemoglobin level sensor, an ultrasound Doppler flow sensor, Laser Doppler Flowmetry ("LDF"), sensors configured to perform measurements of the local optical properties, sensors configured to perform measurements of local electric impedance, sensors configured to perform measurements of the local heat dissipation, etc.

The blood level sensor 504 communicates with the controller 506, whether via a wire, wirelessly, RF, or any other type of communication, and transmits to the controller 506 information regarding local blood perfusion at the insulin infusion site to calculate an adjustment to insulin administration. In some embodiments, the adjustment can be any type of adjustment as described herein, and can be applied to the basal insulin dose and/or to a bolus dose. The insulin adjustment or the new adjusted insulin level is transmitted, either through a wire, wirelessly, RF or any other type of communication, to the drug delivery device 502. In some embodiments, the drug delivery device can apply the adjusted drug level and correct the delivered drug levels according to the calculated adjustments. In some embodiments, the drug delivery device can be an insulin pump and the drug is insulin. The adjusted drug level information, blood level measurements, etc., can be displayed on a user interface 508, which is similar to the user interface 216 and/or the user interface 408 discussed above. As previously discussed, in some embodiments, part or all of the described components are disposed in the same housing.

Any of the exemplary embodiments of the systems shown in FIG. 1, 2, 4 or 5 can be combined into a single system. For example, in embodiments, where the infused drug is insulin, any of these embodiments can be combined using a procedure illustrated in FIG. 3.

Figure 6:
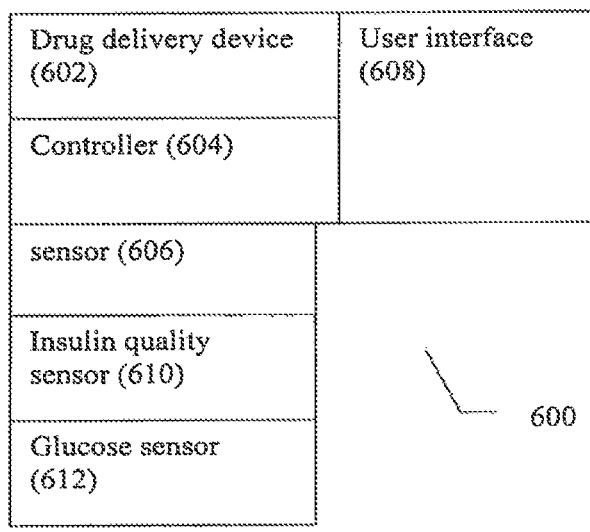
FIG. 6 is a block diagram of another exemplary system that includes a drug delivery device and an insulin quality sensor for providing information about the drug, according to some embodiments of the present invention.

FIG. 6 is a block diagram of an exemplary system 600 that provides information about the drug itself, according to some embodiments of the present invention. In some embodiments, the drug is insulin. The system 600 includes an insulin delivery device 602 for delivering insulin to a subject (not shown in FIG. 6). The system 600 also includes a controller 604 for controlling at least one aspect of insulin administration. In some embodiments, the controller 604 is disposed in the insulin delivery device 602. Alternatively, in some embodiments, the controller 604 is external to the insulin delivery device 602. The controller 604 can be configured to receive information about one or more physiological and/or biochemical and/or environmental parameters from at least one sensor, such as, a sensor 606. Additional sensors can be used in conjunction with the system. The information transmitted by the at least one sensor 606 is used to adjust at least one aspect of drug (e.g., insulin) administration in a manner similar to that previously described in relation to other system embodiments.

In some embodiments, the system 600 also includes an insulin information interface 608. The user can enter the insulin concentration and/or insulin type manually to the insulin information interface 608 to enable accurate determination of the dose adjustment to be computed by the controller 604. In some embodiments, the insulin information interface 608 can scan or read the insulin concentration and/or insulin type anchor insulin expiration date from the insulin package directly (not shown), whether through some type of optical acquisition and recognition mechanism and/or through communication with, for example, an REID (radio frequency identification) device. This feature can help reduce user errors stemming from erroneous entering of insulin concentration data or insulin type data.

In some embodiments, the insulin package or bottle includes a specific code that specifies the insulin type and/or the insulin concentration and/or insulin expiration date, such that the code can be automatically read by the insulin information interface 608 using, for example, codes on packages such as barcodes, optical codes or information encoded using RFID. In some embodiments, the insulin information interface 608 and/or controller 604 is configured to read the code that identifies insulin type and/or insulin concentration and/or insulin expiration date. In some embodiments, the controller 604 receives this information and uses it in the calculation of suitable insulin dosages and/or delivery profile.

In some exemplary embodiments, in the event that it is determined that the expiry date of the insulin has passed, the controller 604 can be configured to alert the user and prevent delivery of the expired insulin. In some embodiments, the user displaces or directs the insulin information interface 608 to the package code as part of filling or replacing the insulin cartridge or insulin reservoir at the insulin delivery device 602. In some embodiments, the insulin delivery device 602 (e.g., an insulin pump) can be configured to request from the user information relating to the new insulin information code and present it to the system's reader (such as an optical reader) (not shown in FIG. 6). The system's reader can be configured to read and appropriately receive the information about the new insulin and enable it to be used.

In some embodiments, a radiofrequency device, such as an RFID device, can be incorporated into the insulin information interface 608 for reading insulin information embedded into an RF code. In this case, when the insulin package is brought in close proximity to the insulin information interface 608, the required insulin information encoded in the RF code (e.g., insulin type and/or the insulin concentration, insulin expiration date, etc.) can be transmitted automatically and without direct physical contact. The insulin data can then be used to enable insulin dose/delivery profile calculations and/or prevent usage of expired insulin.

The insulin package can include one or more authenticity markers to prevent counterfeiting of insulin. Suitable authenticity markers include, for example, holograms, complex barcodes and/or encrypted RFIDs. In the event counterfeited insulin has been detected by the system 600, the controller 604 prevents the insulin delivery device 602 from delivering the insulin to the patient or even from taking up the insulin for delivery. In some embodiments, the insulin delivery device 602 can be configured to prevent insulin delivery without obtaining the required insulin information after insulin refill or replacement.

In some embodiments, the system 600 can include an insulin quality sensor 610 to measure level of insulin deterioration. The insulin deterioration can be measured, for example, using a chemical sensor or an immunoassay, such as an iso-insulin immunoassay manufactured by Merkodia, that can measure the level of active insulin. Such an insulin quality sensor 610 can be disposed in the insulin cartridge or insulin reservoir of the insulin delivery device 602 (not shown in FIG. 6) and can perform the insulin quality measurement after insulin refill or replacement. The insulin quality sensor device also can periodically verify that the insulin has not deteriorated before or during use.

Insulin deterioration may also be measured using an optical sensor for insulin quality sensor 610. An optical sensor that enables insulin quality measurements can measure the optical scattering or absorption of the insulin in the insulin cartridge or reservoir. For example, if small insulin clots or small insulin crystals form in the drug container (e.g., a cartridge), the insulin optical scattering is increased at an early stage of particle formation. The optical scattering and/or absorption of the insulin material can be measured using an optical sensor disposed in and/or out of the insulin cartridge or insulin reservoir at the insulin delivery device 602. The insulin deterioration can be determined after insulin refill or replacement, or occasionally by the insulin delivery device to verify that the insulin has not deteriorated before or during its use by the insulin delivery device 602. In the event that insulin deterioration has been identified, the controller 604 can be configured to initiate an alert to the user that can be visually displayed and/or audio sound so that the user can replace the insulin, check what caused that deterioration and/or report to the insulin supplier.

In circumstances in which the system 600 performs automatic insulin information retrieval, the insulin information interface 608 may be disposed in a third unit, such as a PDA, a cellular telephone, a personal computer, a device for diabetes management such as Personal Diabetes Manager ("PDM") or any other processor-based device. Insulin information, calculated insulin dose or delivery profile and/or any additional relevant information is transmitted to the insulin delivery device 602 via an electrical conductive wire or wirelessly.

In some embodiments, the system 600 can also receive additional information that can be used to compute a recommended insulin dose for the user, whether a basal insulin dose or bolus insulin dose and/or delivery profile. The additional information can include one or more of the current glucose level, the historical glucose profile, meal ingredients or any other parameters germane to computation of the required insulin dose or rate.

In some embodiments, the system 600 can further include a glucose sensor or any other type of sensor 612 to determine the level of glucose or other parameter in the subject. Such information can be used in conjunction with the above described information to determine at least one aspect of insulin administration. One or more of the parameters described herein, including the skin temperature, the ambient temperature, physical activity information, local blood perfusion information, etc., can be used in the course of determining at least one aspect of insulin administration.

In some embodiments, the user enters the insulin infusion site (i.e., location on the patient's body) to the insulin information interface 608 such that the calculation for a specific infusion site can be used to more accurately estimate the dose adjustment. In some embodiments, the insulin dose adjustment is time-dependent and relates to the time passed from the insulin bolus delivery or the time of day. In some embodiments, the insulin dose adjustment calculation can be fine-tuned to personally fit or to be better calibrated for a specific user.

In some embodiments, the infusion rate or dose of other substances which are delivered by a drug delivery device can be adjusted in the same manner as described in relation to the delivery of insulin. Such other substances include pain relief medication(s), hormone(s), and/or other medication(s) that require infusion of an accurate dosage or when accurate blood concentration of the substances profiles is needed.

Figure 7:
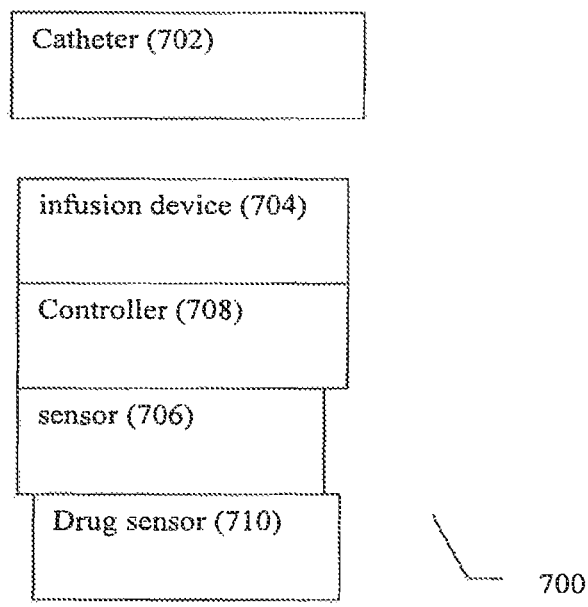
FIG. 7 is a block diagram an exemplary device for drug delivery, according to some embodiments of the present invention.

FIG. 7 is a block diagram of an exemplary drug delivery device 700 having an infusion catheter 702 for insertion into tissue, an infusion device 704 for infusion of a drug into the infusion catheter 702, and at least one sensor 706 for measuring an additional parameter, such as a skin temperature, an ambient temperature, a physical activity information, a local blood perfusion information and the like, according to some embodiments of the present invention. Such additional parameters can be configured to improve and/or stabilize the drug pharmacokinetics, pharmacodynamics, and/or to reduce variations of the drug absorption into the blood system. In some embodiments, the information from sensor 706 can be provided to a controller 708 configured to function in a manner similar to the functionality of the controller described in relation to FIGS. 2, 4, 5 and 6.

In some embodiments, an additional sensor, such as a drug sensor 710, can be included with the device 700 to retrieve at least one drug parameter, such as, the drug type, drug concentration, drug expiration date and/or drug authenticity, to improve and/or stabilize the drug pharmacokinetics or pharmacodynamics, and/or to reduce variations of the drug absorption into the blood system and/or prevent the usage of expired and/or counterfeit drug.

Although particular embodiments have been disclosed herein in detail, this has been done by way of example and for purposes of illustration only, and is not intended to be limiting. In particular, various substitutions, alterations, and modifications may be made without departing from the spirit and scope of the invention. Other aspects, advantages, and modifications are considered to be within the scope of the claims. The claims presented hereafter are merely representative of some of the embodiments of the invention disclosed herein. Other, presently unclaimed embodiments are also contemplated.

Any and all patents, patent applications, articles and other published and non-published documents referred to any where in the subject disclosure are herein incorporated by reference in their entirety.

What is claimed is:

1. An apparatus to control administration of a drug to the body of a patient, the apparatus comprising:
    a drug infusion device configured to deliver the drug at a predetermined location on the body of the patient;
    at least one sensor disposed in the drug infusion device and configured to measure a property related to the patient, wherein the property is a combination of a physiological property related to the patient, a biochemical property related to the patient, including a drug level in the blood of the patient and/or a rate of change of drug level in the blood of the patient, an environmental property related to the patient, including an ambient temperature, and a drug-related property, including quality of the drug being administered;
    a controller disposed in the drug infusion device and configured to receive from the at least one sensor data representative of the measured property and further configured to determine a drug delivery rate or dose based on the received data;
    the drug delivery device is further configured to deliver the drug to the body of the patient based on the determined drug delivery rate or dose; and
    a user interface in communication with the controller and configured to receive input data to enable control of any one of: the quantity of the administered drug, timing of administration of a single dose of the drug, timing of administration of a plurality of doses of the drug, rate administration of a single dose of the drug and timing of administration of a plurality of doses of the drug.

2. The apparatus according to claim 1, wherein the drug is insulin and the input data includes at least one of: timing of the meal, meal composition, physical activity and illness status.

3. The apparatus according to claim 1, wherein the controller is configured to adjust the drug delivery rate or dose based on the input data.

4. The apparatus according to claim 1, wherein the controller is configured to increase the drug delivery rate at a first hour of a carbohydrate rich meal and/or decrease the drug delivery rate at a first hour of a fat rich meal.

5. The apparatus according to claim 1, wherein the user interface is configured to enable the user or any other individual to view data received from the at least one sensor.

6. The apparatus according to claim 1, wherein the drug is a pain relief drug and the input data comprises a level of pain or data related to the effect of the pain relief drug.

7. An apparatus to control administration of a drug to the body of a patient, the apparatus comprising:
    a drug infusion device configured to deliver the drug at a predetermined location on the body of the patient;
    at least one sensor disposed in the drug infusion device and configured to measure a property related to the patient, wherein the property is a combination of a physiological property related to the patient, a biochemical property related to the patient, including a drug level in the blood of the patient and/or a rate of change of drug level in the blood of the patient, an environmental property related to the patient, including an ambient temperature, and a drug-related property, including quality of the drug being administered;
    a controller disposed in the drug infusion device and configured to receive from the at least one sensor data representative of the measured property and further configured to determine a drug delivery rate or dose based on the received data; and
    the drug delivery device is further configured to deliver the drug to the body of the patient based on the determined drug delivery rate or dose, said received data used to detect disconnection or leakage of the drug from the infusion device.

8. The apparatus according to claim 7, wherein the sensor comprises a skin temperature sensor, and the disconnection or leakage is determined based on detection of variations of the skin temperature sensor.

9. The apparatus according to claim 7, wherein the measured property comprises a state of the patient selected from any one of: a high level of physical activity, medium level of physical activity, low level of physical activity or sleep, the controller being configured to adjust the drug delivery rate or dose, based on the state of the patient.

* * * * *